United States Patent
Shandilya et al.

(10) Patent No.: US 7,560,261 B2
(45) Date of Patent: Jul. 14, 2009

(54) NUCLEIC ACID SEQUENCES ENCODING CEL II ENDONUCLEASE

(75) Inventors: Harini Shandilya, Bethesda, MD (US); Gary F. Gerard, Frederick, MD (US); Peter Qiu, Gaithersburg, MD (US)

(73) Assignee: Transgenomic, Inc., Omaha, NE (US)

( * ) Notice: Subject to any disclaimer, the term of this patent is extended or adjusted under 35 U.S.C. 154(b) by 161 days.

(21) Appl. No.: 11/628,726

(22) PCT Filed: May 18, 2005

(86) PCT No.: PCT/US2005/017508

§ 371 (c)(1),
(2), (4) Date: Feb. 2, 2007

(87) PCT Pub. No.: WO2006/007124

PCT Pub. Date: Jan. 19, 2006

(65) Prior Publication Data

US 2007/0231904 A1  Oct. 4, 2007

Related U.S. Application Data

(60) Provisional application No. 60/580,450, filed on Jun. 17, 2004.

(51) Int. Cl.
*C07H 21/00* (2006.01)
*C12N 15/00* (2006.01)
*C12N 5/10* (2006.01)
*C12N 1/21* (2006.01)
*C07K 14/00* (2006.01)
*C12N 9/16* (2006.01)
*C12Q 1/44* (2006.01)
*C12P 21/00* (2006.01)

(52) U.S. Cl. ............... 435/196; 435/320.1; 435/252.3; 435/325; 435/69.1; 435/19; 530/350; 536/23.2

(58) Field of Classification Search ............. 435/196, 435/320.1, 325, 252.3, 69.1, 19; 530/350; 536/23.2

See application file for complete search history.

(56) References Cited

U.S. PATENT DOCUMENTS 5,869,245 A  2/1999  Yeung ............... 435/6
6,391,557 B1  5/2002  Yeung ............... 435/6
6,699,980 B1  3/2004  Yeung ............... 536/23.1
2004/0166510 A1  8/2004  Gerard et al. ......... 435/6

OTHER PUBLICATIONS

Phillips, A., J. Pharm. Pharmacology 53:1169-1174, 2001.*
Gardlik et al., Med. Sci. Monit. 11(4):RA110-121, 2005.*
Kappel et al., Current Opinion in Biotechnology 3:548-553, 1992.*
Mullins et al., Hypertension 22(4):630-633, 1993.*
Mullins et al., J. Clin. Invest. 97(7):1557-1560, 1996.*
Wigley et al., Reprod. Fert. Dev. 6:585-588, 1994.*
Cameron, E., Molecular Biotechnology 7:253-265, 1997.*
Brandon et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Yang et al., "Purification, Cloning, and Characterization of the CEL I Nuclease", Biochemistry 2000 39:3553-3541.
Oleykowski et al., "Mutation detection using a novel plant endonuclease", Nucleice Acids Researc 1998 36(20):4597-4602.
Perez-Amador et al., "Identification of BFN1, a Bifunctional Nuclease Induced during Leaf and Stem Senescence in Arabidopsis", Plant Physiology 2000 122:169-179.
Abler et al., Database Genbank, Feb. 23, 2000, Database accession No. EU90266, the entire document, hybridize to SEQ ID NO: 1 and 3.
NCBI Genbank Accession No. NP_680734 [gi: 22328857] with Revision History, Aug. 20, 2002-Jun. 9, 2006.
NCBI Genbank Accession No. CAC33831 ]gi:13274190] with Revision History, Mar. 6, 2001-Apr. 15, 2005.
NCBI Genbank Accession No. AAC34856 [gi:3551956] with Revision History, Aug. 12, 1998-Jul. 15, 1999.
NCBI Genbank Accession No. BAB03377 [gi:9558456] with Revision History, Jul. 27, 2000-Oct. 5, 2004.
NCBI Genbank Accession No. AAD00695 [gi:4099835] with Revision History, Jan. 5, 1999-Feb. 23, 2000.
Oleykowski et al., "Mutation detection using a novel plant endonuclease", Nucleic Acids Research 1998 26 (20):4597-4602.
Yang et al., "Purification, Cloning and Characterization of the CEL I Nuclease", Biochemistry 2000 39:3533-3541.

* cited by examiner

*Primary Examiner*—Delia M Ramirez
(74) *Attorney, Agent, or Firm*—Licata & Tyrrell P.C.

(57) ABSTRACT

The present invention relates to isolated nucleic acid sequences encoding CEL II endonuclease and vectors and host cells for producing a protein encoded thereby.

8 Claims, 1 Drawing Sheet

```
                          xxkqghfaixkixqxf
CEL II 1  MGMLTYTGIYFLLLL----PSVFCWGKQGHFAICKIAQGFLSKDALTAVK
          |.....::||||.      |.|..|.|:||...|:|||..|..:|..|||
CEL I  1     MTRLYSVFFLLLALVVEPGVRAWSKEGHVMTCQIAQDLLEPEAAHAVK
                                         *

47  ALLPEYADGDLAAVCSWADEVR--FHMRWSSPLHYVDTPDFRCNYKYCRD
           .|||:||:|:|:::|.|.|::|   :..||:|.||::|||..|::.|.||
       49  MLLPDYANGNLSSLCVWPDQIRHWYKYRWTSSLHFIDTPDQACSFDYQRD
                           *                            #
                                          xnnxtealm
       95  CHDSVGRKDRCVTGAIHNYTEQLLLGVHDLNSKMNNNLTEALMFLSHFVG
           |||..|.||.||.|||.|:|.||....|. .|....|:||||:|||||:|
       99  CHDPHGGKDMCVAGAIQNFTSQLGHFRHG-TSDRRYNMTEALLFLSHFMG
           #           #

145  DVHQPLHVGFLGDEGGNTITVRWYRRKTNLHHVWDTMMIESSLKTFYNSD
           |:|||:||||..|.|||:|.:||:|.|:||||||||..:|.::...:..|
      148  DIHQPMHVGFTSDMGGNSIDLRWFRHKSNLHHVWDREIILTAAADYHGKD

195  LSSLIQAIQSNIT-GVWLTDSLSWSNCTADHVVCPDPYASESIELACKFA
           :.||:.||.|.|  |.||.|..||..|. |....|.:.||.|||:|||.:.
      198  MHSLLQDIQRNFTEGSWLQDVESWKECD-DISTCANKYAKESIKLACNWG
                                 *        *               #

244  YRNATPGTTLGDEYFLSRLPVAEKRLAQAGVRLAATLNRIFTSNPSDLTR
           |::...|.||.|:||..:|:|...||:|.|.||:..|||:...|:.....
      247  YKDVESGETLSDKYFNTRMPIVMKRIAQGGIRLSMILNRVLGSSADHSLA

294  LNMHNGGHRSSNNIEIV       310
```

NUCLEIC ACID SEQUENCES ENCODING CEL II ENDONUCLEASE

INTRODUCTION

This application claims the benefit of U.S. Provisional Application No. 60/580,450 filed Jun. 17, 2004, which is herein incorporated by reference in its entirety.

BACKGROUND OF THE INVENTION

A novel family of DNA mismatch-specific endonucleases from plants was discovered recently (Oleykowski, et al. (1998) *Nucl. Acid Res.* 26:4597-4602; Yang, et al. (2000) *Biochem.* 39:3533-3541). The plant source with the highest apparent concentration of this class of endonucleases is celery (Oleykowski, et al. (1998) supra), and thus the enzyme was purified from celery and named CEL I (Oleykowski, et al. (1998) supra; Yang, et al. (2000) supra). CEL I cleaves DNA at the 3'-side of sites of base-substitution mismatch and DNA distortion (Oleykowski, et al. (1998) supra; Yang, et al. (2000) supra).

CEL I has been shown to be useful in mismatch detection assays that rely on nicking or cleaving duplex DNA at insertion/deletion and base-substitution mismatches (Oleykowski, et al. (1998) supra; Yang, et al. (2000) supra; Kulinski, et al. (2000) *BioTechniques* 29:44-48; Colbert, et al. (20001) *Plant Physiol.* 126:480-484; Sokurenko, et al. (2001) *Nucl. Acids Res.* 29:e111; U.S. Pat. No. 5,869,245).

Purified preparations of CEL nuclease identified as CEL I contain two different protein species, CEL I and CEL II (Yang, et al. (2000) supra; U.S. Pat. No. 5,869,245). One species, called CEL I, has an apparent molecular weight of 43 kDa as determined by SDS-PAGE. Removal of N-linked oligosaccharides with Endo $H_f$ reduces the molecular weight to 29 kDa. CEL I was partially sequenced and the gene encoding CEL I was isolated from a celery cDNA library, sequenced, and cloned into *E. coli* (Yang, et al. (2000) supra; U.S. Pat. No. 5,869,245). CEL II has an apparent molecular weight of 39 kDa as determined by SDS-PAGE and removal of N-linked oligosaccharides reduces the molecular weight to 37 kDa. Chromatographic separation of CEL I and CEL II has been described and while CEL I and CEL II appear to be related, they have different enzymatic activity; CEL II has a higher pH optimum than CEL I and CEL II is more efficient than CEL I in cleaving DNA at mismatches.

Therefore, needed in the art is a readily available source of isolated CEL II, which lacks CEL I contamination, for use in detecting the presence of mismatches in double-stranded DNA. The present invention meets this long-felt need in providing nucleic acid sequences encoding CEL II for recombinant production of the same.

SUMMARY OF THE INVENTION

The present invention relates to an isolated nucleic acid encoding a CEL II polypeptide. Said isolated nucleic acid is:
(a) a nucleotide sequence of SEQ ID NO:1 or SEQ ID NO:3;
(b) a nucleotide sequence that hybridizes to a nucleotide sequence of SEQ ID NO:1 or its complementary nucleotide sequence under stringent conditions, wherein said nucleotide sequence encodes a functional CEL II polypeptide; or
(c) a nucleotide sequence encoding an amino acid sequence encoded by the nucleotide sequences of (a) or (b), but which has a different nucleotide sequence than the nucleotide sequences of (a) or (b) due to the degeneracy of the genetic code or the presence of non-translated nucleotide sequences.

The present invention further relates to a vector containing an isolated nucleic acid encoding a CEL II polypeptide.

The present invention further relates to an isolated CEL II polypeptide having an amino acid sequence with at least about 70% amino acid sequence similarity to an amino acid sequence of SEQ ID NO:2 or SEQ ID NO:4, or a functional fragment thereof.

The present invention further relates to a host cell containing an isolated nucleic acid or vector encoding a CEL II polypeptide or a polypeptide encoded thereby.

BRIEF DESCRIPTION OF THE DRAWINGS

FIG. 1 shows the amino acid sequence of CEL II (SEQ ID NO:2) aligned with the sequence of CEL I (SEQ ID NO:5). The peptide leader sequence is underlined and the amino acid sequences determined from the proteolytic peptide fragments of CEL II are shown in lower case letters (SEQ ID NO:6 and SEQ ID NO:7). The nine conserved residues known to be ligands for Zn atom binding are shown in bold italics. The four conserved cys residues shared with P1 nuclease and CEL I are shown with # underneath. The four additional cys residues shared with CEL I are shown with * underneath.

DETAILED DESCRIPTION OF THE INVENTION

Purified preparations of CEL nuclease, generally referred to as CEL I, contain two species of CEL nuclease, CEL I and CEL II (Yang, et al. (2000) supra). A modified purification method from celery was developed that separated the two enzymes. The procedure is summarized herein and in Table 3. CEL II purified in accordance with this method was free of apparent contamination by CEL I, but was contaminated with two proteins or family of proteins that migrated as broad bands at 45 and 57 KDa. After taking this contamination into consideration, the specific activities of the CEL II purified by the purification method were $2.3 \times 10^8$ and $0.21 \times 10^8$ units/mg at pH 8.5 and 5.5, respectively. Gel filtration through SEPHACRYL™ S-100 HR removed most of these contaminants. CEL II eluted from SEPHACRYL™ S-100 HR at a position consistent with a molecular weight of 35.5 KDa. When CEL II was treated with a reducing agent (e.g., β-mercaptoethanol) to break disulfide bridges before being subjected to SDS-PAGE, the protein migrated as two bands at ~16 and ~28 KDa. If CEL II was not exposed to reducing agent, it migrated during SDS-PAGE as expected at ~35 KDa. This was attributed to a break in the CEL II polypeptide backbone introduced by proteolytic cleavage during purification of CEL II. Most CEL II purified by the modified purification method was proteolytically cut at this location. Occasionally some CEL II was obtained that was not cleaved. This break in the backbone did not affect the functional mismatch cutting activity of the enzyme.

CEL I purified by this method was free of apparent contamination by CEL II, but was contaminated with the same two proteins present in CEL II, although to a lesser degree. After taking this contamination into consideration, the specific activity of the purified CEL I was $1.2 \times 10^8$ and $0.8 \times 10^8$ units/mg at pH 5.5 and 8.5, respectively. Known preparations of CEL I nuclease contain both CEL I and CEL II and have a specific activity of $3.1 \times 10^7$ units/mg (Yang, et al. (2000) supra). CEL I migrated at a position on SDS-PAGE consistent with a molecular weight of ~39 KDa. CEL I was not proteolytically clipped during purification.

The enzymatic properties of purified CEL II were subsequently analyzed. In some cases, comparison was made to the properties of CEL I purified with the method disclosed herein. The pH optima in the DNase solubilization assay of CEL I and CEL II are shown in Table 1. CEL I preferred pH 6.0-7.0 and CEL II had optimal activity above pH 9.0. The enzymatic properties of CEL I purified by the method disclosed herein were similar to those of CEL I purified in accordance with known methods (Yang, et al. (2002) supra).

TABLE 1

| pH | DNase Solubilization Activity (Units) | | Relative Activity Setting Value at pH 5.5 at One | |
|---|---|---|---|---|
|  | CEL I | CEL II | CEL I | CEL II |
| 4.5 | 1 | 1 | 0.03 | 0.17 |
| 5.0 | 8 | 2 | 0.25 | 0.33 |
| 5.5 | 32 | 6 | 1.0 | 1.0 |
| 6.0 | 66 | 8 | 2.1 | 1.3 |
| 7.0 | 67 | 30 | 2.1 | 5.0 |
| 8.0 | 50 | 103 | 1.6 | 17.2 |
| 9.0 | 40 | 132 | 1.25 | 22 |
| 9.5 | —$^a$ | 148 | —$^a$ | 24.7 |
| 10.0 | —$^a$ | 215 | —$^a$ | 35.8 |
| 10.5 | —$^a$ | 116 | —$^a$ | 19.3 |

$^a$not determined

Utilizing the mismatched oligonucleotide assay the single-base mismatch cutting preference of purified CEL I and CEL II was found to be the same: C/T~A/C~C/C>T/T>A/A~G/G>>A/G~G/T. The ability of CEL II to cut various distortions in PCR amplified DNA fragments was also examined. When mutant and reference PCR products were hybridized in equal amounts, two alternate heteroduplex mismatches were formed that represent ~50% of the DNA in the mixture. CEL II produced a double-strand cut in every mismatched pair tested in the 632-bp substrate, including G/G and C/C, G/A and T/C, G/T and A/C, and A/A and T/T. Switching the mismatched base in the top and bottom strands such that the mismatches were A/G and C/T or T/G and C/A gave similar cutting efficiencies. Further, CEL II cleaved efficiently at a site in 632-bp substrate containing an insertion of 1 bp, 2 bp, 3 bp, 6 bp, 9 bp, or 12 bp, producing the expected cleavage products in each case. Comparison of the amounts of products generated by CEL II clearly demonstrated that the enzyme cleaves insertions/deletions more efficiently than single-base mismatches. Using the G/G and C/C heteroduplex, the efficiency of cutting the heteroduplex by CEL I and CEL II was compared. Digestion products were fractionated and quantified by HPLC. CEL II was more efficient than CEL I at cutting the mismatch. Approximately 40 units (pH 5.5) of CEL I (14 fmoles) and 10 units (pH 8.5) of CEL II (2.5 fmoles) were required to cut 400 ng of the heteroduplex to the same extent.

The ~16 and ~28 KDa fragments of CEL II were isolated and the amino terminal amino acid sequence of each fragment was determined and are provided herein as SEQ ID NO:6 and SEQ ID NO:7, respectively (FIG. 1). Based upon amino acid sequence homology with the CEL I gene, the 16 KDa fragment was derived from the amino end of the CEL II protein and the 28 KDa fragment was derived from the carboxy end of the protein. Degenerate oligonucleotide primers were designed from these sequences and nucleic acid sequences encoding part of the CEL II gene were cloned. Subsequently, a celery cDNA library was constructed and the full-length CEL II gene was isolated from the library using the overlapping oligonucleotide primers designed from the CEL II partial DNA sequence. The nucleic acid sequence encoding CEL II is provided as SEQ ID NO:1 and the amino acid sequence, including the peptide leader, as SEQ ID NO:2. The nucleic acid sequence encoding CEL II lacking the nucleic acid sequences encoding the 5' untranslated region and the peptide leader is provided as SEQ ID NO:3 and the amino acid sequence, lacking the peptide leader, as SEQ ID NO:4. Including the peptide leader, CEL II and CEL I are 45% identical at the amino acid level (FIG. 1). Starting with the conserved trp at the amino end of the mature protein, CEL II and CEL I contained 291 and 274 amino acids, respectively. The calculated molecular weight of CEL II, without post-translational modification, was 32,629 daltons while CEL I had a calculated molecular weight of 31,440 daltons. The calculated molecular weights of the CEL II ~16 KDa and ~28 KDa fragments were 12.3 and 20.3 KDa, respectively, indicating that both fragments were glycosylated. As with CEL I (Yang, et al. (2000) supra), the nine conserved amino acid residues known to be ligands for binding three catalytically essential Zn atoms in P1 nuclease were present in CEL II (FIG. 1). Both CEL II and CEL I contained the four conserved cys residues present in P1 nuclease that participate in cys-cys bridge formation. In addition, CEL II and CEL I contained four other cys residues at conserved locations and CEL II contained an extra cys residue not shared by CEL I.

The region in the CEL II polypeptide backbone proteolytically cleaved (Leu-Leu-Gly-Val-His-Asp-Leu-Asn-Ser-Lys-Met↓Asn-Asn-Asn-Leu; SEQ ID NO:8) is one of the least conserved regions relative to the corresponding amino acid sequence of CEL I (Gly-His-Phe-Arg-His-Gly-Thr-Ser-Asp-Arg-Arg-Tyr-Asn-Met; SEQ ID NO:9) with only 3 of 13 amino acids conserved. The regions directly adjacent to this divergent region were much more highly conserved (9 of 13 amino acids conserved upstream and 11 of 13 conserved downstream) (FIG. 1). Based upon comparison to the 3-D structure of P1 nuclease, this divergent stretch of amino acids sits on the surface of the enzyme in an exposed loop. The combination of an exposed loop structure and the appropriate amino acid recognition sequence unique to CEL II renders this site susceptible to proteolytic cleavage in CEL II but not in CEL I.

Based on the distinct enzymatic activity of CEL II and its utility in assays for detecting the presence of mismatches in double-stranded DNA, it is desirable to produce highly pure preparations of CEL II on a large scale. Accordingly, the present invention provides an isolated nucleic acid containing a nucleotide sequence encoding a CEL II polypeptide. As used herein, an isolated molecule (e.g., an isolated nucleic acid such as genomic DNA, RNA or cDNA or an isolated polypeptide) means a molecule separated or substantially free from at least some of the other components of the naturally occurring organism, such as for example, the cell structural components or other polypeptides or nucleic acids commonly found associated with the molecule. When the isolated molecule is a polypeptide, said polypeptide is at least about 25%, 50%, 60%, 70%, 75%, 80%, 85%, 90%, 95%, 97%, 98%, 99% or more pure (w/w).

In one embodiment, the nucleotide sequence encoding a CEL II polypeptide is a nucleotide sequence of SEQ ID NO:1 or SEQ ID NO:3. In another embodiment, the nucleotide sequence encoding a CEL II polypeptide is a nucleotide sequence that hybridizes to a nucleotide sequence of SEQ ID NO:1 or its complementary nucleotide sequence under stringent conditions, wherein said nucleotide sequence encodes a functional CEL II polypeptide. In a further embodiment, the nucleotide sequence encoding a CEL II polypeptide is a nucleotide sequence encoding a functional CEL II polypeptide but which has a different nucleotide sequence than the nucleotide sequences of SEQ ID NO:1 or SEQ ID NO:3 due to the degeneracy of the genetic code or the presence of non-translated nucleotide sequences.

As used herein, a functional polypeptide is one that retains at least one biological activity normally associated with that polypeptide. Alternatively, a functional polypeptide retains all of the activities possessed by the unmodified polypeptide. By retains biological activity, it is meant that the polypeptide retains at least about 10%, 20%, 30%, 40%, 50%, 60%, 75%, 85%, 90%, 95%, 97%, 98%, 99%, or more, of the biological activity of the native polypeptide (and can even have a higher level of activity than the native polypeptide). A non-functional polypeptide is one that exhibits essentially no detectable biological activity normally associated with the polypeptide (e.g., at most, only an insignificant amount, e.g., less than about 10% or even 5%).

As used herein, the term polypeptide encompasses both peptides and proteins, unless indicated otherwise.

A CEL II polypeptide or CEL II protein as used herein, is intended to be construed broadly and encompasses an enzyme capable of cleaving double-stranded DNA at base pair mismatches. The term CEL II also includes modified (e.g., mutated) CEL II that retains biological function (i.e., have at least one biological activity of the native CEL II protein, e.g., cleaving double-stranded DNA at base pair mismatches or binding double-stranded DNA at base pair mismatches), functional CEL II fragments including truncated molecules and functional CEL II fusion polypeptides (e.g., an CEL II-GST protein fusion or CEL II-His tagged protein).

Any CEL II polypeptide or CEL II-encoding nucleic acid is considered a CEL II of the present invention. The CEL II polypeptide or CEL II-encoding nucleic acid can be derived from fungi, mammals or other plant species including *Arabidopsis*, Zinnia, alfalfa, asparagus, tomato, cauliflower, broccoli, cabbage, fennel, kale, water cress, parsley, lettuce, mung bean sprouts, *Hemerocallis, Oryza, Hordeum*, or *Zea*. CEL II endonucleases are intended to include endonuclease enzymes of similar activity, pH optima, and size isolated from other non-recombinant or natural sources besides celery.

Representative cDNA sequences of a celery CEL II are provided as SEQ ID NO:1 and SEQ ID NO:3 and representative amino acid sequences are provided as SEQ ID NO:2 and SEQ ID NO:4, respectively. Other CEL II sequences encompassed by the present invention include, but are not limited to, GENBANK accession numbers AAD00695, BAB03377, AAC34856, CAC33831 and NP_680734.

To illustrate, hybridization of such sequences can be carried out under conditions of reduced stringency, medium stringency or even stringent conditions (e.g., conditions represented by a wash stringency of 35-40% Formamide with 5×Denhardt's solution, 0.5% SDS and 1×SSPE at 37° C.; conditions represented by a wash stringency of 40-45% Formamide with 5×Denhardt's solution, 0.5% SDS, and 1×SSPE at 42° C.; and/or conditions represented by a wash stringency of 50% Formamide with 5×Denhardt's solution, 0.5% SDS and 1×SSPE at 42° C., respectively) to the sequences specifically disclosed herein. See, e.g., Sambrook et al., *Molecular Cloning, A Laboratory Manual* (2d Ed. 1989) (Cold Spring Harbor Laboratory).

Alternatively stated, isolated nucleic acids encoding CEL II in accordance with the invention have at least about 60%, 70%, 80%, 90%, 95%, 97%, 98% or higher sequence similarity with the isolated nucleic acid sequences specifically disclosed herein (or fragments thereof, as defined above) and encode a functional CEL II as defined herein.

It will be appreciated by those skilled in the art that there can be variability in the nucleic acids that encode the CEL II of the present invention due to the degeneracy of the genetic code. The degeneracy of the genetic code, which allows different nucleic acid sequences to code for the same polypeptide, is well-known in the literature (see Table 2).

TABLE 2

| Amino Acid | 3-Letter Code | 1-Letter Code | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

Further variation in the nucleic acid sequence can be introduced by the presence (or absence) of non-translated sequences, such as intronic sequences and 5' and 3' untranslated sequences.

Moreover, the isolated nucleic acids of the invention encompass those nucleic acids encoding CEL II polypeptides that have at least about 60%, 70%, 80%, 90%, 95%, 97%, 98% or higher amino acid sequence identity with the polypeptide sequences specifically disclosed herein (or fragments thereof) and further encode a functional CEL II as defined herein.

As is known in the art, a number of different programs can be used to identify whether a nucleic acid or polypeptide has sequence identity or similarity to a known sequence. Sequence identity and/or similarity can be determined using standard techniques known in the art, including, but not limited to, the local sequence identity algorithm of Smith & Waterman (1981) *Adv. Appl. Math.* 2:482, by the sequence identity alignment algorithm of Needleman & Wunsch (1970) *J. Mol. Biol.* 48:443, by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux, et al. (1984) *Nucl. Acid Res.* 12:387-395, either using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360; the method is similar to that described by Higgins & Sharp (1989) *CABIOS* 5:151-153.

Another example of a useful algorithm is the BLAST algorithm, described in Altschul, et al. (1990) *J. Mol. Biol.* 215: 403-410 and Karlin, et al. (1993) *Proc. Natl. Acad. Sci. USA* 90:5873-5787. A particularly useful BLAST program is the WU-BLAST-2 program which was obtained from Altschul, et al. (1996) *Methods in Enzymology*, 266:460-480. WU-BLAST-2 uses several search parameters, which can be set to the default values. The parameters are dynamic values and are established by the program itself depending upon the composition of the particular sequence and composition of the particular database against which the sequence of interest is being searched; however, the values can be adjusted to increase sensitivity.

An additional useful algorithm is gapped BLAST as reported by Altschul, et al. (1997) *Nucleic Acids Res.* 25:3389-3402.

A percentage amino acid sequence identity value can be determined by the number of matching identical residues divided by the total number of residues of the longer sequence in the aligned region. The longer sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the shorter sequence in the aligned region and multiplying by 100. The longer sequence is the one having the most actual residues in the aligned region.

To modify CEL II amino acid sequences specifically disclosed herein or otherwise known in the art, amino acid substitutions can be based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are made in the amino acid sequence encoding CEL II. Such modifications can be made to alter the pH optimum, temperature optimum or stability of CEL II.

In making amino acid substitutions, the hydropathic index of amino acids may be considered. The importance of the hydropathic amino acid index in conferring interactive biologic function on a protein is generally understood in the art (see, Kyte and Doolittle (1982) *J. Mol. Biol.* 157:105). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle (1982) supra), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Isolated nucleic acids of this invention include RNA, DNA (including cDNAs) and chimeras thereof. The isolated nucleic acids can further contain modified nucleotides or nucleotide analogs.

The isolated nucleic acids encoding CEL II can be associated with appropriate expression control sequences, e.g., transcription/translation control signals and polyadenylation signals.

It will be appreciated that a variety of promoter/enhancer elements can be used depending on the level and cell- or tissue-specific expression desired. The promoter can be constitutive or inducible (e.g., the metallothionein promoter or a hormone inducible promoter), depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest. In particular embodiments, the promoter functions in cells that can be used to express nucleic acids encoding CEL II for the purposes of large-scale protein production. Likewise, the promoter can be specific for these cells and tissues (i.e., only show significant activity in the specific cell or tissue type).

To illustrate, a CEL II coding sequence can be operatively associated with a cytomegalovirus (CMV) major immediate-early promoter, an albumin promoter, an Elongation Factor 1-α (EF1-α) promoter, a PγK promoter, a MFG promoter, a Rous sarcoma virus promoter, or a glyceraldehyde-3-phosphate promoter.

Moreover, specific initiation signals are generally required for efficient translation of inserted protein coding sequences. These translational control sequences, which can include the ATG initiation codon and adjacent sequences, can be of a variety of origins, both natural and synthetic. For example, it can be appreciated by one of skill in the art that the expression of CEL II lacking the endogenous signal peptide would require the addition of an initiation codon at the 5' end of the coding sequence for recombinant expression of the mature CEL II protein.

CEL II can be expressed not only directly, but also as a fusion protein with a heterologous polypeptide, i.e. a signal sequence for secretion and/or other polypeptide which will aid in the purification of CEL II. In one embodiment, the heterologous polypeptide has a specific cleavage site to remove the heterologous polypeptide from CEL II.

In general, a signal sequence can be the endogenous signal sequence encoded by SEQ ID NO:1 or can be a component of the vector and should be one that is recognized and processed (i.e., cleaved by a signal peptidase) by the host cell. For production in a prokaryote, a prokaryotic signal sequence from, for example, alkaline phosphatase, penicillinase, lpp, or heat-stable enterotoxin II leaders can be used. For yeast secretion, one can use, e.g., the yeast invertase, alpha factor, or acid phosphatase leaders, the *Candida albicans* glucoamylase leader (EP 362,179), or the like (see, for example WO 90/13646). In mammalian cell expression, signal sequences from secreted polypeptides of the same or related species, as well as viral secretory leaders, for example, the herpes simplex glycoprotein D signal can be used. Such signal sequences can advantageously be fused to nucleic acid sequences coding for the mature CEL II protein (e.g., SEQ ID NO:3).

Other useful heterologous polypeptides which can be fused to CEL II include those which increase expression or solubility of the fusion protein or aid in the purification of the fusion protein by acting as a ligand in affinity purification. Typical fusion expression vectors include pGEX (Amersham Biosciences, Piscataway, N.J.), pMAL (New England Biolabs, Beverly, Mass.) and pRIT5 (Pharmacia, Piscataway, N.J.) which fuse GST, maltose E binding protein or protein A, respectively, to the target recombinant protein.

The isolated nucleic acids encoding CEL II can be incorporated into a vector, e.g., for the purposes of cloning or other laboratory manipulations, recombinant protein production, or gene delivery. In particular embodiments, the vector is an expression vector. Exemplary vectors include bacterial artificial chromosomes, cosmids, yeast artificial chromosomes, phage, plasmids, lipid vectors and viral vectors. By the term express, expresses or expression of a nucleic acid coding sequence, in particular a CEL II coding sequence, it is meant that the sequence is transcribed, and optionally, translated. Typically, according to the present invention, transcription and translation of the coding sequence will result in production of CEL II polypeptide.

The methods of the present invention provide a means for delivering, and optionally expressing, nucleic acids encoding CEL II in a broad range of host cells, including both dividing and non-dividing cells in vitro (e.g., for large-scale recombinant protein production) or in vivo (e.g., for recombinant large-scale protein production or for therapeutic purposes). In embodiments of the invention, the nucleic acid can be expressed transiently in the target cell or the nucleic acid can be stably incorporated into the target cell, for example, by integration into the genome of the cell or by persistent expression from stably maintained episomes (e.g., derived from Epstein Barr Virus).

An isolated nucleic acid encoding CEL II can be expressed by a cell or subject so that CEL II is produced and purified therefrom, i.e., as a source of recombinant CEL II protein. According to this embodiment, the CEL II is secreted into the systemic circulation or into another body fluid (e.g., milk, lymph, spinal fluid, urine) that is easily collected and from which the CEL II can be further purified. As a further alternative, CEL II protein can be produced in avian species and deposited in, and conveniently isolated from, egg proteins.

Likewise, CEL II-encoding nucleic acids can be expressed transiently or stably in a cell culture system for the purpose of screening assays or for large-scale recombinant protein production. The cell can be a bacterial, protozoan, plant, yeast, fungus, or animal cell.

In particular embodiments, an isolated nucleic acid encoding CEL II can be introduced into a cultured cell, e.g., a cell of a primary or immortalized cell line for recombinant protein production. The recombinant cells can be used to produce the CEL II polypeptide, which is collected from the cells or cell culture medium. Likewise, recombinant protein can be produced in, and optionally purified from an organism (e.g., a microorganism, animal or plant) being used essentially as a bioreactor.

Generally, the isolated nucleic acid is incorporated into an expression vector (viral or nonviral). It will be apparent to those skilled in the art that any suitable vector can be used to deliver the isolated nucleic acids of this invention to the target cell(s) or subject of interest. The choice of delivery vector can be made based on a number of factors known in the art, including age and species of the target host, in vitro vs. in vivo delivery, level and persistence of expression desired, intended purpose (e.g., for large-scale production), the target cell or organ, route of delivery, size of the isolated nucleic acid, safety concerns, and the like.

Suitable vectors include virus vectors (e.g., retrovirus, alphavirus; vaccinia virus; adenovirus, adeno-associated virus, or herpes simplex virus), lipid vectors, poly-lysine vectors, synthetic polyamino polymer vectors that are used with nucleic acid molecules, such as plasmids, and the like.

As used herein, the term viral vector or viral delivery vector can refer to a virus particle that functions as a nucleic acid delivery vehicle, and which contains the vector genome packaged within a virion. Alternatively, these terms can be used to refer to the vector genome when used as a nucleic acid delivery vehicle in the absence of the virion.

Protocols for producing recombinant viral vectors and for using viral vectors for nucleic acid delivery can be found in *Current Protocols in Molecular Biology*, Ausubel, F. M. et al. (eds.) Greene Publishing Associates, (1989) and other standard laboratory manuals (e.g., Vectors for Gene Therapy. In: *Current Protocols in Human Genetics*. John Wiley and Sons, Inc.: 1997).

Expression vectors compatible with various host cells are well-known in the art and contain suitable elements for transcription and translation of nucleic acids. Typically, an expression vector contains an expression cassette, which includes, in the 5' to 3' direction, a promoter, a coding sequence encoding an CEL II operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E.*

*coli*, insect cells (e.g., in the baculovirus expression system), yeast cells or mammalian cells. Some suitable host cells are discussed further in Goeddel (1990) Gene Expression Technology: Methods in Enzymology 185, Academic Press, San Diego, Calif. Examples of vectors for expression in yeast *S. cerevisiae* include pYepSec1 (Baldari, et al. (1987) *EMBO J.* 6:229-234), pMFa (Kurjan and Herskowitz (1982) *Cell* 30:933-943), pJRY88 (Schultz, et al. (1987) *Gene* 54:113-123), and pYES2 (INVITROGEN Corporation, San Diego, Calif.). Baculovirus vectors available for expression of nucleic acids to produce proteins in cultured insect cells (e.g., Sf 9 cells) include the pAc series (Smith, et al. (1983) *Mol. Cell. Biol.* 3:2156-2165) and the pVL series (Lucklow and Summers (1989) *Virology* 170:31-39).

Examples of mammalian expression vectors include pCDM8 (Seed (1987) *Nature* 329:840) and pMT2PC (Kaufman, et al. (1987) *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

In addition to the regulatory control sequences discussed herein, the recombinant expression vector can contain additional nucleotide sequences. For example, the recombinant expression vector can encode a selectable marker gene to identify host cells that have incorporated the vector.

Vectors can be introduced into prokaryotic or eukaryotic cells via conventional transformation or transfection techniques. As used herein, the terms transformation and transfection refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, *Agrobacterium*-mediated transformation, gene bombardment using high velocity microprojectiles, and viral-mediated transfection. Suitable methods for transforming or transfecting host cells can be found in Sambrook, et al. (Molecular Cloning: A Laboratory Manual, 2nd Edition, Cold Spring Harbor Laboratory press (1989)), and other laboratory manuals.

Often only a small fraction of cells (in particular, mammalian cells) integrate the foreign DNA into their genome. In order to identify and select these integrants, a nucleic acid that encodes a selectable marker (e.g., resistance to antibiotics) can be introduced into the host cells along with the nucleic acid of interest. In particular embodiments, selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

Recombinant proteins can also be produced in a transgenic plant in which the isolated nucleic acid encoding the protein is inserted into the nuclear or plastidic genome. Vectors, plants, cell culture and methods for transforming plants and plant cells are known as the art. See, in general, *Methods in Enzymology* Vol. 153 (Recombinant DNA Part D) 1987, Wu and Grossman Eds., Academic Press and European Patent Application EP 693554.

In plant cells, expression systems are often derived from recombinant Ti and Ri plasmid vector systems. In the cointegrate class of shuttle vectors, the gene of interest is inserted by genetic recombination into a non-oncogenic Ti plasmid that contains both the cis-acting and transacting elements required for plant transformation. Exemplary vectors include the pMLJ1 shuttle vector (DeBlock, et al. (1984) *EMBO J.* 3:1681-1689) and the non-oncogenic Ti plasmid pGV2850 (Zambryski, et al. (1983) *EMBO J.* 2:2143-2150). In the binary system, the gene of interest is inserted into a shuttle vector containing the cis-acting elements required for plant transformation. The other necessary functions are provided in trans by the non-oncogenic Ti plasmid. Exemplary vectors include the pBIN19 shuttle vector (Bevan (1984) *Nucl. Acids Res.* 12:8711-8721) and the non-oncogenic Ti plasmid pAL4404 (Hoekema, et al. (1983) *Nature* 303:179-180). Alternatively, CEL II nucleic acid sequences can be introduced, with the appropriate regulatory sequences, into plant cells via biolistic transformation.

Promoters used in plant expression systems are typically derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV). Expression of CEL II sequences in plants can be constitutive or temporally- or spatially-regulated. Exemplary plants for expressing CEL II include, but are not limited to tobacco (e.g. expression in leaves), maize (e.g., expression in seeds), or potato (e.g., expression in tubers). Expression in plant cell lines is further contemplated.

The present invention further provides cultured or recombinant cells containing the isolated nucleic acids encoding CEL II for use in the screening methods and large-scale protein production methods of the invention (e.g., CEL II is produced and collected from the cells and, optionally, purified).

CEL II can also be produced in vivo in animals. Thus, as still a further aspect, the invention provides a transgenic non-human animal containing an isolated nucleic acid encoding CEL II, which can be produced according to methods well-known in the art. The transgenic non-human animal can be any species, including avians and non-human mammals. According to this aspect of the invention, suitable non-human mammals include mice, rats, rabbits, guinea pigs, goats, sheep, pigs and cattle.

A nucleic acid encoding CEL II is stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells contain and express the CEL II transgene.

Methods of making transgenic animals are known in the art. DNA constructs can be introduced into the germ line of an avian or mammal to make a transgenic animal. For example, one or several copies of the construct can be incorporated into the genome of an embryo by standard transgenic techniques.

In an exemplary embodiment, a transgenic non-human animal is produced by introducing a transgene into the germ line of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the transgene into the embryo can be accomplished by any of a variety of means known in the art such as microinjection, electroporation, lipofection or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgenic construct into the fertilized egg, the egg can be incubated in vitro for varying amounts of time, or reimplanted into the surrogate host, or both. One common method is to incubate the embryos in vitro for about 1-7 days, depending on the species, and then reimplant them into the surrogate host.

The progeny of the transgenically manipulated embryos can be tested for the presence of the construct (e.g., by Southern blot analysis) of a segment of tissue. An embryo having one or more copies of the exogenous cloned construct stably integrated into the genome can be used to establish a permanent transgenic animal line carrying the transgenically added construct.

Transgenically altered animals can be assayed after birth for the incorporation of the construct into the genome of the offspring. This can be done by hybridizing a probe corresponding to the DNA sequence coding for the polypeptide or a segment thereof onto chromosomal material from the progeny. Those progeny found to contain at least one copy of the construct in their genome are grown to maturity.

Methods of producing transgenic avians are also known in the art, see, e.g., U.S. Pat. No. 5,162,215.

For large-scale production, CEL II polypeptides can be purified from cultured cells or transgenic animals. Typically, the polypeptide is recovered from the culture medium of bodily fluid (e.g., mild or egg) as a secreted polypeptide, although it also can be recovered from host cell lysates when directly expressed without a secretory signal. When CEL II is expressed in a recombinant cell other than one of celery origin, the CEL II is completely free of proteins or polypeptides of celery origin. However, it is necessary to purify CEL II from recombinant cell proteins or polypeptides to obtain preparations that are substantially homogeneous as to CEL II. As a first step, the culture medium or lysate is centrifuged to remove particulate cell debris. The membrane and soluble protein fractions are then separated. The CEL II can then be purified from the soluble protein fraction. CEL II thereafter can then be purified from contaminant soluble proteins and polypeptides as disclosed herein or with, for example, the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX™ G-75; and ligand affinity chromatography.

Suitably pure preparations of CEL II can be analyzed for CEL endonuclease activity using one or more well-known assays including, but not limited to, a DNA nicking assay, a DNase solubilization assay, or a mismatch endonuclease assay. Purified products can also be analyzed by electrophoretic separation, such as polyacrylamide gel electrophoresis.

Purified CEL II preparations can be used in methods for detecting the presence of mismatches in double-stranded DNA or determining the site of a mutation in double-stranded DNA mismatches in double-stranded DNA. Examples of such methods are found in U.S. Pat. Nos. 5,869,245 and 6,027,898. It is contemplated that CEL II produced from nucleic acid sequences, vectors and host cells disclosed herein can be used in methods for analyzing a sample of double-stranded DNA to determine the presence of a mutation therein. Such a method involves contacting a sample (e.g., a biological sample, cells, tissue, etc.) containing double-stranded DNA with an isolated CEL II endonuclease, separating the product of the CEL II endonuclease digestion, and detecting said product. An increase in the number of fragments (i.e., CEL II digestion of one band into two or more bands as determined on an agarose gel) or decrease in the size of the DNA in the presence of the CEL II endonuclease is indicative of a mismatch in said DNA. The step of separating the product of the CEL II endonuclease digestion may be carried out using gel electrophoresis, capillary electrophoresis, or chromatographic separation such as Matched Ion Polynucleotide Chromatography, size exclusion chromatography, ion exchange chromatography, or reverse phase chromatography. Standard methods of detecting a DNA molecule are well-known in the art (e.g., ethidium bromide staining or UV absorbance; labeling with a radioactive isotope or a fluorophore).

The invention is described in greater detail by the following non-limiting examples.

EXAMPLE 1

Materials and Assays

Materials. Calf thymus DNA (SIGMA, St Louis, Mo.) was purified by repeated cycles of proteinase K treatment and phenol extraction, reduced in viscosity by sonication, and denatured by heating in a boiling water bath for 10 minutes followed by quick cooling on wet ice. Q SEPHAROSE™ Fast Flow, Heparin SEPHAROSE™ Fast Flow, G-25 SEPHADEX™, SEPHACRYL™ S-100 HR, and ConA-SEPHAROSE™ matrices, as well as HIPREP™ 16/10 Heparin SEPHAROSE™ Fast Flow, MONO S™ HR 5/5, HITRAP™ Heparin HP, and MONO Q™ HR 5/5 columns were from AMERSHAM™ PHARMACIA™ Biotech (Piscataway, N.J.). Synthetic oligonucleotides were from INVITROGEN™ (Carlsbad, Calif.).

DNA Sequencing. Individual *E. coli* colonies were grown overnight in liquid culture at 37° C. Plasmid DNAs were isolated using the Plasmid Miniprep Kit (QIAGEN®, Valencia, Calif.) and the appropriate gene was sequenced using the ABI 3100 Genetic Analyzer (ABI, Foster City, Calif.).

Mismatch Cutting Assay with PCR Fragments. Plasmid pQIS155 contains a derivative of the gene for CEL I (Yang, et al. (2000)) cloned between the NdeI and XhoI sites of pET22b (NOVAGEN®, Madison, Wis.). Using a GENETAILOR™ Site-Directed Mutagenesis System (INVITROGEN™, Carlsbad, Calif.), the C at position 605, called the target site, in the CEL I gene of pQIS155 was changed to A, G, and T, or insertions of 1, 2, 3, 6, 9, and 12 bases were made at the site. Plasmid DNAs were transformed into *E. coli* DH5α (INVITROGEN™, Carlsbad, Calif.) and cells were grown in LB medium+100 μg/mL ampicillin. Plasmid DNA was isolated using a Plasmid Mini Kit (QIAGEN®, Valencia, Calif.). Plasmids were named based upon their sequence at the target site, e.g., pQIS155G has a G at the target site.

A 632-bp fragment was amplified from pQIS155 plasmid DNA and its derivatives utilizing the following primers (INVITROGEN™, Carlsbad, Calif.): pCELR: 5'-CGC CAA AGA ATG ATC TGC GGA GCT T-3' (SEQ ID NO:10) and pCEL190F: 5'-ACA CCT GAT CAA GCC TGT TCA TTT GAT TAC-3' (SEQ ID NO:11). PCR was performed with OPTIMASE® Polymerase (Transgenomic, Omaha, Nebr.) utilizing the recommended reaction conditions. The amount and quality of the amplified DNA produced in a PCR reaction were determined by visual comparison of the DNA product to a DNA mass ladder (NEB, Beverly, Mass.) fractionated by agarose gel electrophoresis. Heteroduplexes were formed by annealing equal amounts of amplified DNA prepared from pQIS155 and one of its derivatives. DNA hybridization was performed in a thermocycler using the following program: 95° C. for 10 minutes; 95° C. to 85° C. at −2° C./s; and 85° C. to 25° C. at −0.1° C./s. When two different alleles are annealed in a 1:1 mixture mismatch heteroduplexes are formed approximately 50% of the time. For each base change, two mismatches are formed. Reformed homoduplexes constitute the other 50% of the population.

Annealed DNA (200 ng) was digested using 5 units (pH 8.5) of CEL II in a 20-μL volume containing 20 mM Tris-HCl, pH 7.4, 25 mM KCl, 10 mM $MgCl_2$, and 100 units of T4 DNA ligase. Annealed DNA (200 ng) can also be digested by direct addition of 5 units of CEL II nuclease to the DNA in 1×PCR buffer. The digestion reaction was incubated at 42° C. for 20 minutes and was stopped by addition of 2 μL of 0.5 M EDTA. Cleavage products were fractionated on a 2% agarose gel cast and run in 1×TAE buffer (40 mM Tris-acetate, pH 8.3, 1 mM EDTA). The gel was stained with ethidium bromide and photographed over UV transillumination.

Annealed DNA (400 ng) to be analyzed by HPLC was digested using the desired amounts of CEL I or CEL II in a 40-μL volume containing 20 mM Tris-HCl, pH 7.4, 25 mM KCl, and 10 mM $MgCl_2$. Annealed DNA (400 ng) can also be digested with the desired amounts of CEL I or CEL II by direct addition of enzyme to the DNA in 1×PCR buffer. The digestion reaction was incubated at 42° C. for 20 minutes and was stopped by addition of 4 μL of 0.5 M EDTA. Cleavage products (40 μL) generated were separated on a WAVE system using UV detection at 260 nm (Transgenomic, Omaha, Nebr.). The DNASEP® Cartridge was run at 50° C. under non-denaturing conditions to separate DNA fragments based upon size.

DNase Solubilization Assay. Two solubilization assays were carried out at pH 5.5 and 8.5. Reaction mixtures (50 μL) at pH 5.5 contained 20 mM sodium acetate (pH 5.5), 10 mM KCl, 0.5 mg/mL denature calf thymus DNA, and various amounts of CEL nuclease. Reaction mixtures at pH 8.5 contained the same components except the buffer was 20 mM Tris-HCl (pH 8.5), 10 mM KCl, and 3 mM $MgCl_2$. Reactions were incubated at 37° C. for 10 minutes and were terminated by the addition of 50 μL of cold 20 mM $LaCl_3$ in 0.2 N HCl. After 10 minutes on ice and centrifugation in an EPPENDORF® microfuge at 13,000 rpm for 10 minutes, the absorbance at 260 nm of the supernatant was measured in a spectrophotometer to determine the amount of DNA solubilized. One unit of solubilization activity (a CEL Nuclease Unit) is the amount of enzyme required to produce 1 ng of acid-soluble material in 1 minute at 37° C.

Mismatch Cutting Assay with Oligonucleotides. A mismatch endonuclease assay was performed using standard methods (Oleykowski, et al. (1998) supra) using matched and mismatched DNA 64-mer duplexes as described by Oleylowski et al. ((1998) supra) in FIG. 1B therein. The duplexes used were blunt-ended. When desired DNA oligonucleotides were labeled at the 5' end with [γ-$^{32}$P]ATP and T4 polynucleotide kinase (Sambrook, et al. (Molecular Cloning: A Laboratory Manual, 2nd Edition, Cold Spring Harbor Laboratory press (1989)). Reaction mixtures (20 μL) for the mismatch endonuclease assay contained 20 mM Tris-HCl (pH 7.4), 25 mM KCl, 10 mM $MgCl_2$, 500 ng unlabeled DNA 64-mer duplex or 5 ng 5'-end labeled duplex, and CEL nuclease. When labeled duplex was used, Taq DNA polymerase (2.5 units; PROMEGA®, Madison Wis.) was added and incubation was at 42° C. for 5 minutes. When unlabeled duplex was used, incubation was for 30 minutes at 42° C. Proteinase K (2 μg) was added at the end of 30 minutes and incubation was continued for 5 minutes at 42° C. Incubations were terminated by the addition of 1.5 μL of 70% (w/v) sucrose, 50 mM EDTA, 5 mM 1,10 phenanthroline, 0.1% (w/v) xylene cyanol, and 0.4% (w/v) bromophenol blue. The DNA was fractionated on a 12% PAGE gel. Unlabeled DNA was run on gels containing no urea and the gel was stained with ethidium bromide and photographed using a KODAK™ EDAS 290 System with the gel illuminated by a UV transilluminator at 254 nm. Labeled DNA was run on gels both without and containing 7 M urea. The gels were dried and the radioactivity was analyzed on a PHOSPHORIMAGER™ (MOLECULAR DYNAMICS™, Sunnyvale Calif.).

SDS-Polyacrylamide Gel Electrophoresis (SDS-PAGE). SDS-PAGE (Sambrook, et al. (1989) supra) was carried out in 14% or 10-20% precast polyacrylamide gels (INVITROGEN™, Carlsbad, Calif.). Protein was concentrated by TCA precipitation followed by acetone washing prior to heating in SDS sample buffer. Protein bands were detected by silver stain (BIO-RAD®, Hercules, Calif.). MARK 12™ (INVITROGEN™, Carlsbad, Calif.) protein standards were run to establish molecular weights.

Protein Concentration Determination. The concentration of proteins was determined using the Bicinchoninic acid protein assay (Pierce, Rockford, Ill.) with bovine serum albumin as a standard.

EXAMPLE 2

Purification of CEL Nucleases

All steps were performed at 4° C. During column chromatography the nuclease activity was monitored with DNase solubilization assays performed at pH 5.5 and 8.5.

Preparation of Crude Extract. Chilled Celery Stalks (15-20 bunches) were minced in a food processor and homogenized in a WARING® blender. The juice was collected from the pulp by squeezing the pulp to dryness through 4 layers of cheesecloth. The juice was centrifuged at 5,000×g for 20 minutes to remove green particulate material. The clarified amber-colored juice was adjusted to the composition of ConA Buffer (100 mM Tris-HCl, pH 7.7, 100 μM phenylmethyl sulfonyl fluoride (PMSF)) by the addition of 1 M Tris-HCl (pH 7.7) and 0.1 M PMSF. Solid $(NH_4)_2SO_4$ was added to the juice to 80% of saturation (51.6 g/100 mL) and the suspension was stirred for 2 hours. The suspension was centrifuged at 10,000×g for 30 minutes to recover a tight protein pellet. The pellet was dissolved in 700-800 mL of ConA Buffer. $(NH_4)_2SO_4$ was dissolved to 15% of saturation (8.4 g/100 mL) and the suspension was stirred for 30 minutes. The suspension was centrifuged at 10,000×g for 30 minutes and the pellet was discarded.

Concanavalin A-SEPHAROSE™ Affinity Chromatography. Con A-SEPHAROSE™ (100 mL) (cross-linked with dimethyl suberimidate) was packed into a 2.5-cm diameter column and equilibrated in ConA Wash Buffer (ConA Buffer+0.5 M KCl). The $(NH_4)_2SO_4$ supernatant was loaded onto the column at a flow rate of 0.75 mL/minute overnight. The column was then disassembled and the resin washed in a Buchner funnel with 6-8 liters of ConA Wash Buffer. The washed resin was then repacked into the 2.5-cm column using ConA Wash Buffer. The CEL nucleases were eluted with 100 mL of ConA Wash Buffer+0.5 M α-methyl mannoside. The elution was repeated 4 more time. The eluants were combined and made 0.01% in TRITON™ X-100.

G-25 SEPHADEX™ Chromatography. The ConA-SEPHAROSE™ pool was desalted on a 2 L (10×26 cm) G-25 SEPHADEX™ column equilibrated in Buffer A (50 mM Tris-HCl, pH 8.0, 5 mM α-methyl mannoside, 0.01% TRI- TON™ X-100). The column was developed in Buffer A+100 µM PMSF at 25-30 mL/minute. The protein eluted between 700 and 1,400 ml elution volume and was pooled. The pool was made 50 mM in α-methyl mannoside by the addition of 1 M α-methyl mannoside.

Q SEPHAROSE™ Chromatography. The desalted ConA pool was loaded onto a 50-ml Q SEPHAROSE™ Fast Flow column (2.5×10 cm) equilibrated with Buffer A+45 mM α-methyl-mannoside at ~0.5 mL/minute overnight. The column was washed with 250 mL of Buffer A+45 mM α-methyl mannoside. CEL nucleases were eluted with a 500-mL linear gradient of 0 to 0.5 M KCl in Buffer A+45 mM α-methyl-mannoside. A large peak of DNA exonuclease activity (was active in the solubilization assay at pH 5.5 but not at pH 8.5) was sometimes observed eluting from Q SEPHAROSE™ between 0.05 and 0.12 M KCl. The CEL nucleases eluted between 0.12 and 0.18 M KCl, based upon the pH 5.5 solubilization assay, and between 0.12 and 0.35 M KCl, based upon the pH 8.5 solubilization assay. Fractions were pooled between 0.12 M and 0.35 M KCl, avoiding the exonuclease at low concentrations of KCl and the major protein contaminants at high concentrations of KCl. Pooling above 0.35 M KCl was avoided as the bulk of contaminating proteins eluted as the KCl concentration increased. There was a compromise between pooling all of the CEL II activity (active at pH 8.5) and excluding the contaminating proteins that eluted at higher concentrations of KCl. The CEL I and CEL II were pooled together.

The CEL nuclease peak fractions were pooled and dialyzed against Buffer B (25 mM $KPO_4$, pH 7.0, 5 mM α-methyl mannoside, 0.01% TRITON™ X-100)+100 µM PMSF.

Heparin SEPHAROSE™ Chromatography. The dialyzed CEL nuclease pool from Q SEPHAROSE™ was made 50 mM in α-methyl mannoside and loaded onto a 20-mL HIPREP™ 16/10 Heparin FF column (0.6×18 cm) equilibrated in Buffer B+45 mM α-methyl mannoside at 1 mL/minute. The column washed with 100 mL of Buffer B+45 mM α-methyl mannoside at 2 mL/minute. The CEL nucleases were eluted with a 200-mL linear gradient of 0 to 0.3 M KCl in Buffer B+45 mM α-methyl mannoside+100 µM PMSF at 2 mL/minute with 4 mL/fraction. Fractions were assayed at pH 5.5 and 8.5. CEL I and CEL II were partially separated by Heparin SEPHAROSE™ chromatography. The major peak of protein contaminants eluted at 0.02 to 0.12 M KCl. CEL II (more active at pH 8.5) eluted at 0.06 to 0.18 M KCl. CEL I (more active at pH 5.5) eluted at 0.12 to 0.22 M KCl. CEL II was pooled narrowly on the low concentration of KCl side to avoid protein contamination and on the high concentration of KCl side to avoid CEL I (pool from 0.09 to 0.15 M KCl). CEL I was pooled between 0.15 and 0.21 M KCl. The CEL II purification was subsequently performed.

The CEL I pool was dialyzed overnight against 2 liters of Buffer A+100 µM PMSF and was stored at 4° C. until final purification.

The CEL II pool was dialyzed overnight against 2 liters of Buffer C (10 mM PIPES-NaOH, pH 7.2, 5 mM α-methyl mannoside, 0.01% TRITON™ X-100)+100 µM PMSF in preparation for MONO S™ chromatography.

MONO S™ HR 5/5 Chromatography of CEL II. The dialyzed CEL II pool in Buffer C from the Heparin SEPHAROSE™ column was made 50 mM in α-methyl mannoside by addition of 1 M α-methyl mannoside and the pH was adjusted to 6.2 by the addition of 1 M PIPES (pH 6.0) (~2 mL). The sample was loaded onto a 1-mL MONO S™ HR 5/5 column equilibrated in Buffer D (50 mM PIPES-NaOH, pH 6.2, 5 mM α-methyl mannoside, 0.01% TRITON™ X-100)+ 45 mM α-methyl-mannoside+100 µM PMSF at 0.5 mL/minute. The column washed with 5 mL of Buffer D+45 mM α-methyl mannoside+100 µM PMSF at 1 mL/minute. CEL nucleases were eluted with a 25-mL linear gradient of 0 to 0.3 M KCl in Buffer D+45 mM α-methyl mannoside+100 µM PMSF at 1 mL/minute with 0.5 mL/fraction. Solubilization assays were done at pH 5.5 and 8.5. The major peak of protein contaminants eluted at 0.05 to 0.21 M KCl. CEL I eluted at 0.15 to 0.22 M KCl. CEL II eluted at 0.18 to 0.28 M KCl. CEL II was pooled narrowly between 0.21 and 0.26 M KCl, avoiding as much as possible protein contamination and CEL I on the low concentration of KCl side. After pooling, 1 M Tris-HCl (pH 8.0) was added immediately to bring the pH up to 8.0 (~0.5 mL of Tris added to 3-3.5 mL of pooled enzyme).

The CEL II pool was dialyzed against 1 liter of Buffer A+100 µM PMSF overnight.

MONO Q™ HR 5/5 Chromatography of CEL II. The dialyzed CEL II pool from the MONO S™ column was made 50 mM in α-methyl mannoside and loaded onto a MONO Q™ HR 5/5 column equilibrated in Buffer A+45 mM α-methyl mannoside at 0.5 mL/minute. The column washed with 5 mL of Buffer A+45 mM α-methyl-mannoside at 1 mL/minute. CEL II was eluted with a 25-mL linear gradient of 0 to 0.3 M KCl in Buffer A+45 mM α-methyl mannoside at 1 mL/minute with 0.5 mL/fraction. Solubilization assays were performed at pH 8.5. CEL II eluted between 0.1 and 0.25 M KCl. CEL II was pooled narrowly between 0.1 and 0.18 M KCl to avoid protein contaminants that eluted at higher and lower concentrations of KCl.

The CEL II pool was dialyzed overnight against 1 liter of Storage Buffer (50 mM Tris-HCl, pH 7.5, 100 mM KCl, 10 µM $ZnCl_2$, 0.01% TRITON™ X-100, 50% glycerol) and stored at –20° C.

Dialysis of CEL I Against Buffer C. The CEL I Heparin SEPHAROSE™ pool that was stored in Buffer A at 4° C. was dialyzed overnight against 2 liters of Buffer C+100 µM PMSF before HITRAP™ Heparin HP chromatography.

HITRAP™ Heparin HP Chromatography of CEL I. The dialyzed Heparin SEPHAROSE™ CEL I pool was made 50 mM in α-methyl mannoside and the pH was adjusted to 6.2 by the addition 1 M PIPES (pH 6.0) (~2 mL). The pool was loaded unto a 1-mL HITRAP™ Heparin HP column equilibrated in Buffer D+45 mM α-methyl mannoside at 0.5 mL/minute. The column washed with 5 mL of Buffer D+45 mM α-methyl-mannoside at 1 mL/minute. CEL I was eluted with a 20-mL linear gradient of 0 to 0.5 M KCl in Buffer D+45 mM α-methyl mannoside at 1 mL/minute with 0.5 mL/fraction. Assays were performed at pH 5.5. The major protein contamination peak eluted between 0.1 and 0.38 M KCl. The CEL I eluted between 0.32 and 0.47 M KCl. CEL I was pooled narrowly to avoid the protein contaminants that eluted at lower concentrations of KCl, between 0.35 and 0.45 M KCl. After pooling, 1 M Tris-HCl (pH 8.0) was added immediately to bring the pH up to 8.0 (~0.5 mL of Tris added to 3-3.5 mL of pooled enzyme).

The CEL I pool was dialyzed overnight against 1 liter of Buffer A+100 mM PMSF.

MONO Q™ HR 5/5 Chromatography of CEL I. The dialyzed CEL I pool from HITRAP™ Heparin HP was made 50 mM in α-methyl mannoside and loaded onto a MONO Q™ HR 5/5 column equilibrated in Buffer A+45 mM α-methyl mannoside at 0.5 mL/minute. The column washed with 5 mL of Buffer A+45 mM α-methyl mannoside at 1 mL/minute. CEL I was eluted with a 25-mL linear gradient of 0 to 0.3 M KCl in Buffer A+45 mM α-methyl mannoside at 1 mL/minute with 0.5 mL/fraction. Fractions were assayed at pH 5.5. CEL I eluted between 0.09 and 0.15 M KCl. The peak fractions of CEL I activity were pooled between 0.11 to 0.13 M KCl.

The CEL I pool was dialyzed against Storage Buffer overnight and store at −20° C.

Purification Monitoring. The purification was monitored by carrying out unit and protein determinations on pools from each purification step. The results of such monitoring are shown in Table 3, which shows typical yield and fold-purification results from the purification at each step. In addition, graphs were plotted for each chromatography step in order to make intelligent pooling decisions. These graphs contained profiles for protein concentration, unit activity at pH 5.5 and 8.5, and salt concentration.

SEPHACRYL™ S-100 HR Gel Filtration. CEL II MONO Q™ concentrate (Table 3; 500 μL) was dialyzed against Buffer A+0.15 M NaCl and fractionated on a SEPHACRYL™ S-100 HR column (1.5×28 cm; 50 mL) developed in Buffer A+0.15 M NaCl at 0.25 mL/minute. The column void volume was 18.3 mL. Ovalbumin (43 KDa) eluted at 23.2 mL and CEL II eluted as a sharp peak at 24.5 mL (35.5 KDa).

TABLE 3

| Fraction | Volume (mL) | Protein Conc. (mg/mL) | Total Protein (mg) | Unit Activity (Units/mL)[a] |
|---|---|---|---|---|
| Clarified Crude | 6750 | 7.8 | 52620 | 53,000 (53,000) |
| (NH$_4$)$_2$SO$_4$ | 775 | 8.9 | 6898 | 118,000 (75,000) |
| Con A SEPHAROSE ® Desalted | 650 | 0.41 | 267 | 53,000 (21,000) |
| Q SEPHAROSE ® | 195 | 0.43 | 84 | 45,000 (38,000) |
| Heparin SEPHAROSE ® CEL I | 36 | 0.037 | 1.33 | 69,000 (45,000) |
| Heparin SEPHAROSE ® #2 CEL I | 2.9 | 0.0125 | 0.036 | 270,000 (170,000) |
| MONO Q ™ CEL I | 3.5 | 0.001 | 0.0035 | 50,000 (70,000) |
| MONO Q ™ Concentrate CEL I[b] | 0.9 | 0.0039 | 0.0035 | 380,000 (250,000) |
| Heparin SEPHAROSE ® CEL II | 39 | 0.077 | 3.0 | 21,000 (72,000) |
| MONO S ™ CEL II | 3.4 | 0.015 | 0.051 | 65,000 (360,000) |
| MONO Q ™ CEL II | 5.5 | 0.001 | 0.0055 | 8,000 (83,000) |
| MONO Q ™ Concentrate CEL II[c] | 1.35 | 0.004 | 0.0055 | 21,000 (230,000) |

| Fraction | Total Activity ×10$^5$ (Units) | Specific Activity (Units/mg) | Fold Purification | % Recovery |
|---|---|---|---|---|
| Clarified Crude | 3580 (3580) | 6,800 (6,800) | 1 (1) | 100 (100) |
| (NH$_4$)$_2$SO$_4$ | 1150 (580) | 13,192 (8,408) | 1.9 (1.2) | 25 (16) |
| Con A SEPHAROSE ® Desalted | 345 (137) | 129,213 (51,310) | 19 (7.5) | 9.6 (3.8) |
| Q SEPHAROSE ® | 88 (74) | 104,760 (88,095) | 15.4 (13.0) | 2.4 (2.1) |
| Heparin SEPHAROSE ® CEL I | 25 (16) | 1,879,700 (1,203,010) | 276 (177) | 0.69 (0.45) |
| Heparin SEPHAROSE ® #2 CEL I | 7.8 (4.9) | 21,750,000 (13,694,440) | 3,199 (2,014) | 0.22 (0.14) |
| MONO Q ™ CEL I | 1.75 (2.45) | 50,000,000 (70,000,000) | 7,353 (10,294) | 0.05 (0.07) |
| MONO Q ™ Concentrate CEL I[b] | 3.4 (2.25) | 97,714,430 (64,285,710) | 14,370 (9,453) | 0.1 (0.06) |
| Heparin SEPHAROSE ® CEL II | 8.2 (28) | 273,330 (933,330) | 40.1 (137) | 0.23 (0.78) |
| MONO S ™ CEL II | 2.2 (12.2) | 433,330 (24,000,000) | 64 (3,529) | 0.06 (0.34) |
| MONO Q ™ CEL II | 0.4 (4.6) | 8,000,000 (83,636,360) | 1,176 (12,299) | 0.012 (0.13) |
| MONO Q ™ Concentrate CEL II[c] | 0.3 (3.1) | 5,163,600 (56,454,550) | 759 (8,302) | 0.008 (0.09) |

[a]Solubilization units without parenthesis were determined at pH 5.5 and with parenthesis at pH 8.5.
[b]CEL I was 80% homogeneous as determined by visual inspection of SDS-PAGE gels.
[c]CEL II was 25% homogeneous as determined by visual inspection of SDS-PAGE gels.

EXAMPLE 3

Amino Acid Sequence Determination of CEL II

SDS-PAGE, Electroblotting onto PVDF Membrane, and Amino Acid Analysis. CEL II nuclease (MONO Q™ Concentrated Pool; Table 3) was buffer-exchanged into Dilution Buffer (25 mM Tris-HCl, pH 7.5, 100 mM KCl, 10 μM ZnCl$_2$) and concentrated by using a MICROCON® YM-10 concentrator (AMICON®, Billerica, Mass.). The sample was centrifuged in the concentrator at 12,000 rpm in an EPPENDORF® 5415D microfuge at 4° C. The concentrated protein was precipitated by adding an equal volume of cold 30% TCA and letting the tube sit on ice for 30 minutes. The sample was centrifuged at 12,000 rpm at 4° C. for 10 minutes, the supernatant was discarded, and the pellet washed with cold acetone. The pellet obtained after centrifugation was air-dried and dissolved in SDS-PAGE sample buffer containing β-mercaptoethanol. The sample was separated on a 14% Tris-glycine gel (INVITROGEN™, Carlsbad, Calif.). Proteins were then electro-transferred onto a PVDF membrane at 25 volts (constant voltage) for one hour using 1× Electroblot Buffer (10 mM CAPS, pH 11.0, 10% methanol). The membrane was stained in 0.1% Ponceau S (SIGMA) for 5 minutes and then de-stained in 1% acetic acid. CEL II in the presence of a reducing agent separated as two fragments at ~16 kDa and ~28 kDa. Sections of the PVDF membrane containing each of these bands were cut out and sequenced at the amino terminus The amino terminal amino acid sequence of the fragments of CEL II were:

SEQ ID NO:6,
16 KDa fragment: Xaa-Xaa-Lys-Gln-(Gly)-(His)-Phe-

Ala-Ile-Xaa-Lys-Ile-Xaa-Gln-Xaa-(Phe);
and

SEQ ID NO:7
28 KDa fragment: Xaa-(Asn)-Asn-Xaa-Thr-Glu-Ala-

Leu-Met;

where Xaa indicates the presence of an undefined amino acid and parenthesis indicates some uncertainty.

Based upon amino acid sequence homology with the CEL I gene, the 16 KDa fragment was derived from the amino end of the CEL II protein and the 28 KDa fragment was derived from the carboxy end of the protein. Degenerate oligonucleotide primers were designed from these sequences to clone the CEL II gene from celery cDNA. They were:

```
                                            (SEQ ID NO:12)
(forward primer) 5'-AAR CAR GGH CAY TTY GCH AT-3'
and (SEQ ID NO:13)
(reverse primer) 5'-AAC ATY ARD GCY TCY GT-3', where R = A or G; H = A, C, or T; Y = C or T; and D = A, G, or T.
```

EXAMPLE 4

Isolation CEL II Nucleic Acid Sequences

Isolation of Total RNA from Celery. Total RNA was isolated from frozen celery stalks using the CONCERT™ Plant RNA Reagent (INVITROGEN™, Carlsbad, Calif.) following the small scale RNA isolation protocol. Frozen celery stalks were ground to a powder with a mortar and pestle. Cold Plant RNA Reagent (0.5 mL per 0.1 gm ground tissue) was added to the ground tissue and tubes were incubated at room temperature for 5 minutes. The suspension was clarified by centrifugation at room temperature (12,000×g, 2 minutes). NaCl (5 M; 0.1 mL) was added to the clarified extract and the contents were mixed by gentle inversion. An equal volume of chloroform was added to the tube, the contents were mixed by inversion, and the sample was centrifuged at 4° C. (12,000×g, 10 minutes) to separate the phases. The top, aqueous phase was transferred to a fresh tube and an equal volume of isopropanol was added to the tube. The sample was mixed, allowed to stand at room temperature for 10 minutes, and centrifuged at 4° C. (12,000×g, 10 minutes). The supernatant was decanted and the pellet washed with 75% ethanol. After a brief centrifugation (12,000×g, 2 minutes), the liquid was carefully removed and the pellet was dissolved in RNase-free water. The absorbance at 260 nm was measured and the concentration of the RNA was calculated.

First-Strand cDNA Synthesis and PCR. First-strand cDNA was synthesized using the CREATOR™ SMART™ cDNA Library Construction Kit (CLONTECH™ Laboratories Inc., Palo Alto, Calif.). Total RNA (~1 µg) was annealed with the kit primers SMART™ IV and CDS III/3' PCR Primer by incubating at 65° C. for 5 minutes. The cDNA synthesis reaction (10 µL) containing 1× First Strand Buffer, 2 mM DTT, 1 mM of each dNTP, and POWERSCRIPT™ Reverse Transcriptase was incubated at 42° C. for 60 minutes. Using degenerate oligonucleotides, designed based upon the amino terminal sequences of the CEL II peptides, and the first-strand cDNA as the template, PCR was carried out using the ADVANTAGE® 2 Polymerase Mix (CLONTECH™ Laboratories Inc.). Based upon the projected locations of the amino ends of the CEL II gene fragments, a ~300 to 400 bp 5'-portion of the CEL II gene was predicted. Gel analysis of the amplified product showed a general smear from ~100 bp to ~1,500 bp in length with some specific bands. The DNA smear in the region of 200-400 bp was excised from the gel and the DNA was extracted using the QIAQUICK® Gel Extraction Kit (QIAGEN®, Valencia, Calif.). This was used again as the template for amplification with the degenerate primers in a reaction mixture containing 1× ADVANTAGE® 2 PCR Buffer, 0.2 mM of each dNTP, 0.2 mM of each primer, amplified DNA, and 1× ADVANTAGE® 2 Polymerase Mix. PCR cycling conditions were 10 cycles of 15 seconds at 94° C., 15 seconds at 55° C., and 1 minute at 68° C., followed by 10 cycles of 15 seconds at 94° C., 15 seconds at 50° C., and 1 minute at 68° C., followed by 10 cycles of 15 seconds at 94° C., 15 seconds at 45° C., and 1 minute at 68° C. A specific PCR band ~350 bp in size was observed upon gel analysis and was excised and extracted. The PCR fragment was cloned into the pCR 2.1-TOPO® vector (INVITROGEN™) using the TOPO TA CLONING® Kit. DNA was isolated from 16 colonies and the DNA sequence of each insert was determined using primers complementary to the vector. The DNA sequence of only one out of sixteen when translated had amino acid sequences at the ends that matched the amino acid sequence of the CEL II peptide fragments. The DNA sequence (5' to 3') and the corresponding amino acid sequence obtained for this clone are set forth herein as SEQ ID NO:14 and SEQ ID NO:15, respectively.

cDNA Library Construction. First-strand cDNA was used as the template for making double-stranded cDNA by conducting Long-Distance PCR (LD-PCR) with the CREATOR™ SMART™ cDNA Library Construction Kit (CLONTECH™ Laboratories Inc.). The modified oligo(dT) primer (CDS III/3' PCR Primer) along with the SMART™ IV Oligonucleotide Primer were used to obtain full-length cDNA that contained the complete 5' end of the mRNA. The amplification reaction mixture contained 1× ADVANTAGE® 2 PCR Buffer, 0.2 mM of each dNTP, 0.2 µM of CDC III/3' PCR Primer and 5'PCR Primer, first-strand cDNA, and 1× ADVANTAGE® 2 Polymerase Mix and was cycled for 26 cycles of 5 seconds at 95° C. and 6 minutes at 68° C. The double-stranded cDNA product appeared as a smear when analyzed by agarose gel electrophoresis. The double-stranded cDNA was purified by treatment with proteinase K, phenol extraction, and ethanol precipitation. The purified DNA was digested with SfiI. The DNA was separated on a 1% agarose gel and the DNA smear between ~0.5 kb to 3 kb was extracted from the gel with a QIAQUICK® Gel Extraction Kit. The SfiI-digested, gel purified double-stranded cDNA was ligated with T4 DNA ligase to the SfiI-digested, dephosphorylated PDNR-LIB vector provided in the kit (16° C. overnight). One microliter of the ligation mix was transformed into 50 µL of ONE SHOT® Top10 E. coli electrocompetent cells by electroporation using a BIO-RAD® GENE PULSER®. Five microliters of the transformation mix was plated on LB agar plates containing 30 µg/mL of chloramphenicol and the plates were incubated at 37° C. overnight. The remainder of the transformation mix was stored at 4° C. Analysis of 18 independent clones for the presence of an insert was used to determine the percentage of recombinant clones. The transformation mix was grown at 30° C. in LB+chloramphenicol (30 µg/mL) for a few hours and then inoculated into a larger culture that was grown overnight at 30° C. The culture was centrifuged and the library DNA was isolated from the cell pellet using the Plasmid Midi Prep Kit from QIAGEN®.

Isolation of the CEL II Gene from the cDNA Library. Based upon the partial DNA sequence that was obtained from the 5' end of the CEL II gene, two overlapping oligonucleotides were designed to amplify the CEL II gene from the cDNA library:

```
                                            (SEQ ID NO:16)
forward primer 5'-TT CAT GAC TTG AAT TCA AAA ATG AAT A-3',
and (SEQ ID NO:17)
reverse primer 5'-TGA ATT CAA GTC ATG AAC ACC CAA

TAG-3'.
```

The cDNA library DNA was methylated using the CpG methylase M.SssI (New England Biolabs, Beverly, Mass.). With methylated DNA as the template and the CEL II-specific primers, the cDNA was amplified by PCR in a reaction mixture containing 1× ADVANTAGE® 2 PCR Buffer, 0.2 mM of each dNTP, 0.2 µM of each primer, cDNA, and 1× ADVANTAGE® 2 Polymerase Mix. After initial denaturation at 95° C. for 2 minutes, 30 cycles of 30 seconds at 95° C., 30 seconds at 55° C., and 6 minutes at 68° C. were performed. The overlapping primers generated PCR products containing complementary ends that allowed the products to form circles in vivo. The PCR product was transformed into *E. coli* DH5α cells and plated on LB agar plates containing chloramphenicol (30 µg/mL). DH5α cells contain a wild-type copy of the mcrBC gene that degrades DNA in cells containing methylated cDNA template preventing their growth and allows cells containing PCR amplified DNA to grow. Colonies were screened for the presence of the CEL II gene by digesting the miniprep DNA with EcoRI. From the DNA sequence of the CEL II gene, an EcoRI site ~310 bp from the 5' end of the gene coding for processed protein (after removal of the signal peptide) was predicted. DNAs from clones yielding the expected EcoRI digest pattern were then subjected to DNA sequencing. Out of the 17 clones whose DNA was sequenced, 7 had the sequence of the CEL II gene corresponding to processed protein and one had the full-length sequence corresponding to the protein that included the signal peptide.

What is claimed is:

1. An isolated nucleic acid encoding a CEL II polypeptide comprising SEQ ID NO: 2 or SEQ ID NO: 4.

2. The nucleic acid of claim 1, wherein said nucleic acid comprises:
   (a) a nucleic acid comprising SEQ ID NO: 1 or SEQ ID NO: 3; or
   (b) a nucleic acid that hybridizes under stringent conditions of 5000 Formamide with 5×Denhardt's solution, 0.5% SDS and 1×SSPE at 42° C. to a nucleic acid comprising SEQ ID NO: 1 or SEQ ID NO: 3.

3. A vector comprising the nucleic acid of claim 1.

4. A vector comprising the nucleic acid of claim 2.

5. An isolated host cell comprising the nucleic acid of claim 1.

6. An isolated host cell comprising the nucleic acid of claim 2.

7. An isolated host cell comprising the vector of claim 3.

8. An isolated host cell comprising the vector of claim 4.

* * * * *

UNITED STATES PATENT AND TRADEMARK OFFICE
CERTIFICATE OF CORRECTION

PATENT NO.        : 7,560,261 B1
APPLICATION NO. : 11/628726
DATED             : July 14, 2009
INVENTOR(S)       : Shandilya et al.

It is certified that error appears in the above-identified patent and that said Letters Patent is hereby corrected as shown below:

At col. 35, at line 48, in the Claims:

Claim 2 (b), please delete "5000" and insert --50%--.

Signed and Sealed this

Twenty-fifth Day of August, 2009

David J. Kappos
*Director of the United States Patent and Trademark Office*

SEQUENCE LISTING

<160> NUMBER OF SEQ ID NOS: 17

<210> SEQ ID NO 1
<211> LENGTH: 933
<212> TYPE: DNA
<213> ORGANISM: Apium sp.

<400> SEQUENCE: 1

```
atgggtatgt tgacttatac tggaatttat tttctgctat tacttccaag tgttttctgt      60
tggggaaaac aaggacattt tgcaatttgt aaaattgccc aggggttcct tagtaaagat     120
gcactgactg cagtgaaagc attgctccca gaatatgcag atggtgatct agcagctgtt     180
tgctcctggg ctgacgaggt tcgatttcat atgcgttgga gtagcccatt acattatgtg     240
gacacgcctg atttcaggtg taactataaa tactgtagag attgccatga ttctgttgga     300
cggaaagacc ggtgtgttac tggagcaatt cacaactaca cagagcaact tctattgggt     360
gttcatgact tgaattcaaa aatgaataac aacttgacgg aggcacttat gttcttatca     420
catttcgttg gtgatgtcca tcagcctcta catgttggct tccttggcga tgaaggagga     480
aacacaatca ccgtccgctg gtatcggagg aaaaccaatt tgcatcatgt atgggacaca     540
atgatgattg aatcctcctt gaagacattc tacaattcag atctttctag cttaatacaa     600
gctattcaga gcaatattac aggtgtctgg cttaccgaca gcttatcttg gagcaattgc     660
actgctgatc atgtggtttg tccagacccg tatgcttctg aaagcattga gttggcctgc     720
aagtttgcct acagaaatgc cacacctggg accactttag gagatgagta cttcctctct     780
cggttgcctg ttgcggagaa gaggttggct caggctgggg tccgtttggc tgctactctt     840
aaccgaatct tcacttcaaa ccccagcgat ctcacaagat tgaatatgca taatggtgga     900
catagaagca gtaacaatat tgaaatagtg taa                                  933
```

<210> SEQ ID NO 2
<211> LENGTH: 310
<212> TYPE: PRT
<213> ORGANISM: Apium sp.

<400> SEQUENCE: 2

Met Gly Met Leu Thr Tyr Thr Gly Ile Tyr Phe Leu Leu Leu Leu Pro
1               5                   10                  15

Ser Val Phe Cys Trp Gly Lys Gln Gly His Phe Ala Ile Cys Lys Ile
            20                  25                  30

Ala Gln Gly Phe Leu Ser Lys Asp Ala Leu Thr Ala Val Lys Ala Leu
        35                  40                  45

```
Leu Pro Glu Tyr Ala Asp Gly Asp Leu Ala Ala Val Cys Ser Trp Ala
     50                  55                  60

Asp Glu Val Arg Phe His Met Arg Trp Ser Ser Pro Leu His Tyr Val
 65                  70                  75                  80

Asp Thr Pro Asp Phe Arg Cys Asn Tyr Lys Tyr Cys Arg Asp Cys His
                 85                  90                  95

Asp Ser Val Gly Arg Lys Asp Arg Cys Val Thr Gly Ala Ile His Asn
            100                 105                 110

Tyr Thr Glu Gln Leu Leu Leu Gly Val His Asp Leu Asn Ser Lys Met
                115                 120                 125

Asn Asn Asn Leu Thr Glu Ala Leu Met Phe Leu Ser His Phe Val Gly
130                 135                 140

Asp Val His Gln Pro Leu His Val Gly Phe Leu Gly Asp Glu Gly Gly
145                 150                 155                 160

Asn Thr Ile Thr Val Arg Trp Tyr Arg Arg Lys Thr Asn Leu His His
                165                 170                 175

Val Trp Asp Thr Met Met Ile Glu Ser Ser Leu Lys Thr Phe Tyr Asn
                180                 185                 190

Ser Asp Leu Ser Ser Leu Ile Gln Ala Ile Gln Ser Asn Ile Thr Gly
            195                 200                 205

Val Trp Leu Thr Asp Ser Leu Ser Trp Ser Asn Cys Thr Ala Asp His
        210                 215                 220

Val Val Cys Pro Asp Pro Tyr Ala Ser Glu Ser Ile Glu Leu Ala Cys
225                 230                 235                 240

Lys Phe Ala Tyr Arg Asn Ala Thr Pro Gly Thr Thr Leu Gly Asp Glu
                245                 250                 255

Tyr Phe Leu Ser Arg Leu Pro Val Ala Glu Lys Arg Leu Ala Gln Ala
            260                 265                 270

Gly Val Arg Leu Ala Ala Thr Leu Asn Arg Ile Phe Thr Ser Asn Pro
        275                 280                 285

Ser Asp Leu Thr Arg Leu Asn Met His Asn Gly Gly His Arg Ser Ser
290                 295                 300

Asn Asn Ile Glu Ile Val
305                 310

<210> SEQ ID NO 3
<211> LENGTH: 873
<212> TYPE: DNA
<213> ORGANISM: Apium sp.

<400> SEQUENCE: 3
tggggaaaac aaggacattt tgcaatttgt aaaattgccc aggggttcct tagtaaagat      60
gcactgactg cagtgaaagc attgctccca gaatatgcag atggtgatct agcagctgtt     120
tgctcctggg ctgacgaggt tcgatttcat atgcgttgga gtagcccatt acattatgtg     180
gacacgcctg atttcaggtg taactataaa tactgtagag attgccatga ttctgttgga     240
cggaaagacc ggtgtgttac tggagcaatt cacaactaca cagagcaact tctattgggt     300
gttcatgact tgaattcaaa atgaataac aacttgacgg aggcacttat gttcttatca     360
catttcgttg gtgatgtcca tcagcctcta catgttggct ccttggcga tgaaggagga     420 aacacaatca ccgtccgctg gtatcggagg aaaaccaatt tgcatcatgt atgggacaca     480
atgatgatta atcctccctt gaagacattc tacaattcag atctttctag cttaatacaa     540
gctattcaga gcaatattac aggtgtctgg cttaccgaca gcttatcttg gagcaattgc     600
```

```
actgctgatc atgtggtttg tccagacccg tatgcttctg aaagcattga gttggcctgc      660
aagtttgcct acagaaatgc cacacctggg accactttag agatgagta cttcctctct      720 cggttgcctg ttgcggagaa gaggttggct caggctgggg tccgtttggc tgctactctt      780
aaccgaatct tcacttcaaa ccccagcgat ctcacaagat tgaatatgca taatggtgga      840
catagaagca gtaacaatat tgaaatagtg taa                                  873
```

<210> SEQ ID NO 4
<211> LENGTH: 290
<212> TYPE: PRT
<213> ORGANISM: Apium sp.

<400> SEQUENCE: 4

```
Trp Gly Lys Gln Gly His Phe Ala Ile Cys Lys Ile Ala Gln Gly Phe
1               5                   10                  15

Leu Ser Lys Asp Ala Leu Thr Ala Val Lys Ala Leu Leu Pro Glu Tyr
            20                  25                  30

Ala Asp Gly Asp Leu Ala Ala Val Cys Ser Trp Ala Asp Glu Val Arg
        35                  40                  45

Phe His Met Arg Trp Ser Ser Pro Leu His Tyr Val Asp Thr Pro Asp
    50                  55                  60

Phe Arg Cys Asn Tyr Lys Tyr Cys Arg Asp Cys His Asp Ser Val Gly
65                  70                  75                  80

Arg Lys Asp Arg Cys Val Thr Gly Ala Ile His Asn Tyr Thr Glu Gln
                85                  90                  95

Leu Leu Leu Gly Val His Asp Leu Asn Ser Lys Met Asn Asn Asn Leu
            100                 105                 110

Thr Glu Ala Leu Met Phe Leu Ser His Phe Val Gly Asp Val His Gln
        115                 120                 125

Pro Leu His Val Gly Phe Leu Gly Asp Glu Gly Asn Thr Ile Thr
    130                 135                 140

Val Arg Trp Tyr Arg Arg Lys Thr Asn Leu His His Val Trp Asp Thr
145                 150                 155                 160

Met Met Ile Glu Ser Ser Leu Lys Thr Phe Tyr Asn Ser Asp Leu Ser
                165                 170                 175

Ser Leu Ile Gln Ala Ile Gln Ser Asn Ile Thr Gly Val Trp Leu Thr
            180                 185                 190

Asp Ser Leu Ser Trp Ser Asn Cys Thr Ala Asp His Val Val Cys Pro
        195                 200                 205

Asp Pro Tyr Ala Ser Glu Ser Ile Glu Leu Ala Cys Lys Phe Ala Tyr
    210                 215                 220

Arg Asn Ala Thr Pro Gly Thr Thr Leu Gly Asp Glu Tyr Phe Leu Ser
225                 230                 235                 240

Arg Leu Pro Val Ala Glu Lys Arg Leu Ala Gln Ala Gly Val Arg Leu
                245                 250                 255

Ala Ala Thr Leu Asn Arg Ile Phe Thr Ser Asn Pro Ser Asp Leu Thr
            260                 265                 270

Arg Leu Asn Met His Asn Gly Gly His Arg Ser Ser Asn Asn Ile Glu
        275                 280                 285

Ile Val
    290
```

<210> SEQ ID NO 5
<211> LENGTH: 296

```
<212> TYPE: PRT
<213> ORGANISM: Apium sp.

<400> SEQUENCE: 5

Met Thr Arg Leu Tyr Ser Val Phe Phe Leu Leu Ala Leu Val Val
1               5                   10                  15

Glu Pro Gly Val Arg Ala Trp Ser Lys Glu Gly His Val Met Thr Cys
            20                  25                  30

Gln Ile Ala Gln Asp Leu Leu Glu Pro Glu Ala Ala His Ala Val Lys
        35                  40                  45

Met Leu Leu Pro Asp Tyr Ala Asn Gly Asn Leu Ser Ser Leu Cys Val
    50                  55                  60

Trp Pro Asp Gln Ile Arg His Trp Tyr Lys Tyr Arg Trp Thr Ser Ser
65                  70                  75                  80

Leu His Phe Ile Asp Thr Pro Asp Gln Ala Cys Ser Phe Asp Tyr Gln
                85                  90                  95

Arg Asp Cys His Asp Pro His Gly Gly Lys Asp Met Cys Val Ala Gly
            100                 105                 110

Ala Ile Gln Asn Phe Thr Ser Gln Leu Gly His Phe Arg His Gly Thr
        115                 120                 125

Ser Asp Arg Arg Tyr Asn Met Thr Glu Ala Leu Leu Phe Leu Ser His
    130                 135                 140

Phe Met Gly Asp Ile His Gln Pro Met His Val Gly Phe Thr Ser Asp
145                 150                 155                 160

Met Gly Gly Asn Ser Ile Asp Leu Arg Trp Phe Arg His Lys Ser Asn
                165                 170                 175

Leu His His Val Trp Asp Arg Glu Ile Ile Leu Thr Ala Ala Ala Asp
            180                 185                 190

Tyr His Gly Lys Asp Met His Ser Leu Leu Gln Asp Ile Gln Arg Asn
        195                 200                 205

Phe Thr Glu Gly Ser Trp Leu Gln Asp Val Glu Ser Trp Lys Glu Cys
    210                 215                 220

Asp Asp Ile Ser Thr Cys Ala Asn Lys Tyr Ala Lys Glu Ser Ile Lys
225                 230                 235                 240

Leu Ala Cys Asn Trp Gly Tyr Lys Asp Val Glu Ser Gly Glu Thr Leu
                245                 250                 255

Ser Asp Lys Tyr Phe Asn Thr Arg Met Pro Ile Val Met Lys Arg Ile
            260                 265                 270

Ala Gln Gly Gly Ile Arg Leu Ser Met Ile Leu Asn Arg Val Leu Gly
        275                 280                 285

Ser Ser Ala Asp His Ser Leu Ala
    290                 295

<210> SEQ ID NO 6
<211> LENGTH: 16
<212> TYPE: PRT
<213> ORGANISM: Apium sp.
<220> FEATURE:
<221> NAME/KEY: MISC_FEATURE
<222> LOCATION: (1)..(2)
<223> OTHER INFORMATION: Xaa represents an undefined amino acid residue.
<220> FEATURE:
<221> NAME/KEY: MISC_FEATURE
<222> LOCATION: (10)..(10)
<223> OTHER INFORMATION: Xaa represents an undefined amino acid residue.
<220> FEATURE:
<221> NAME/KEY: MISC_FEATURE
<222> LOCATION: (13)..(13)
<223> OTHER INFORMATION: Xaa represents an undefined amino acid residue.
```

```
<220> FEATURE:
<221> NAME/KEY: MISC_FEATURE
<222> LOCATION: (15)..(15)
<223> OTHER INFORMATION: Xaa represents an undefined amino acid residue.

<400> SEQUENCE: 6

Xaa Xaa Lys Gln Gly His Phe Ala Ile Xaa Lys Ile Xaa Gln Xaa Phe
1               5                   10                  15

<210> SEQ ID NO 7
<211> LENGTH: 9
<212> TYPE: PRT
<213> ORGANISM: Apium sp.
<220> FEATURE:
<221> NAME/KEY: MISC_FEATURE
<222> LOCATION: (1)..(1)
<223> OTHER INFORMATION: Xaa represents an undefined amino acid residue
<220> FEATURE:
<221> NAME/KEY: MISC_FEATURE
<222> LOCATION: (4)..(4)
<223> OTHER INFORMATION: Xaa represents an undefined amino acid residue

<400> SEQUENCE: 7

Xaa Asn Asn Xaa Thr Glu Ala Leu Met
1               5

<210> SEQ ID NO 8
<211> LENGTH: 15
<212> TYPE: PRT
<213> ORGANISM: Apium sp.

<400> SEQUENCE: 8

Leu Leu Gly Val His Asp Leu Asn Ser Lys Met Asn Asn Asn Leu
1               5                   10                  15

<210> SEQ ID NO 9
<211> LENGTH: 14
<212> TYPE: PRT
<213> ORGANISM: Apium sp.

<400> SEQUENCE: 9

Gly His Phe Arg His Gly Thr Ser Asp Arg Arg Tyr Asn Met
1               5                   10

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
cgccaaagaa tgatctgcgg agctt                                             25

<210> SEQ ID NO 11
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 11
acacctgatc aagcctgttc atttgattac                                        30

<210> SEQ ID NO 12
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 12
aarcargghc ayttygchat                                                   20

<210> SEQ ID NO 13
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 13
aacatyardg cytcygt                                                      17

<210> SEQ ID NO 14
<211> LENGTH: 345
<212> TYPE: DNA
<213> ORGANISM: Artificial Sequence
<220> FEATURE:
<223> OTHER INFORMATION: Synthetic amplicon

<400> SEQUENCE: 14
aagcaaggtc attttgctat ttgtaaaatt gcccaggggt tccttagtaa agatgcactg       60
actgcagtga aagcattgct cccagaatat gcagatggtg atctagcagc tgtttgctcc      120
tgggctgacg aggttcgatt tcatatgcgt tggagtagcc cattacatta tgtggacacg      180
cctgatttca ggtgtaacta taaatactgt agagattgcc atgattctgt ggacggaag      240 gaccggtgtg ttactggagc aattcacaac tacacagagc aacttctatt gggtgttcat      300
gacttgaatt caaaaatgaa taacaacttg acagaagcac taatg                      345

<210> SEQ ID NO 15
<211> LENGTH: 138
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: MISC_FEATURE
<222> LOCATION: (8)..(8)
<223> OTHER INFORMATION: Xaa represents an undefined amino acid residue
<220> FEATURE:
<221> NAME/KEY: MISC_FEATURE
<222> LOCATION: (11)..(11)
<223> OTHER INFORMATION: Xaa represents an undefined amino acid residue
<220> FEATURE:
<221> NAME/KEY: MISC_FEATURE
<222> LOCATION: (13)..(13)
<223> OTHER INFORMATION: Xaa represents an undefined amino acid residue
<220> FEATURE:
<221> NAME/KEY: MISC_FEATURE
<222> LOCATION: (130)..(130)
<223> OTHER INFORMATION: Xaa represents an undefined amino acid residue
<220> FEATURE:
<221> NAME/KEY: MISC_FEATURE
<222> LOCATION: (133)..(133)
<223> OTHER INFORMATION: Xaa represents an undefined amino acid residue

<400> SEQUENCE: 15

Lys Gln Gly His Phe Ala Ile Xaa Lys Ile Xaa Gln Xaa Phe Lys Gln
1               5                   10                  15

Gly His Phe Ala Ile Cys Lys Ile Ala Gln Gly Phe Leu Ser Lys Asp
            20                  25                  30

Ala Leu Thr Ala Val Lys Ala Leu Leu Pro Glu Tyr Ala Asp Gly Asp
```

```
                    35                  40                  45
Leu Ala Ala Val Cys Ser Trp Ala Asp Glu Val Arg Phe His Met Arg
    50                  55                  60

Trp Ser Ser Pro Leu His Tyr Val Asp Thr Pro Asp Phe Arg Cys Asn
65                  70                  75                  80

Tyr Lys Tyr Cys Arg Asp Cys His Asp Ser Val Gly Arg Lys Asp Arg
                85                  90                  95

Cys Val Thr Gly Ala Ile His Asn Tyr Thr Glu Gln Leu Leu Leu Gly
            100                 105                 110

Val His Asp Leu Asn Ser Lys Met Asn Asn Leu Thr Glu Ala Leu
        115                 120                 125

Met Xaa Asn Asn Xaa Thr Glu Ala Leu Met
    130                 135

<210> SEQ ID NO 16
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 16
ttcatgactt gaattcaaaa atgaata                                        27

<210> SEQ ID NO 17
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 17
tgaattcaag tcatgaacac ccaatag                                        27
```